(12) United States Patent
Imran (10) Patent No.: US 11,794,001 B2
(45) Date of Patent: Oct. 24, 2023

(54) DEVICE, SYSTEMS AND METHODS FOR TREATMENT OF NEUROGENIC BLADDER

(71) Applicant: InCube Labs, LLC, San Jose, CA (US)

(72) Inventor: Mir Imran, Los Altos Hills, CA (US)

(73) Assignee: InCube Labs, LLC, San Jose, CA (US)

( * ) Notice: Subject to any disclaimer, the term of this patent is extended or adjusted under 35 U.S.C. 154(b) by 903 days.

(21) Appl. No.: 16/668,672

(22) Filed: Oct. 30, 2019

(65) Prior Publication Data

US 2020/0139109 A1 May 7, 2020

Related U.S. Application Data

(60) Provisional application No. 62/754,433, filed on Nov. 1, 2018.

(51) Int. Cl.
*A61N 1/00* (2006.01)
*A61N 1/05* (2006.01)
(Continued)

(52) U.S. Cl.
CPC ............ *A61N 1/0514* (2013.01); *A61F 2/042* (2013.01); *A61M 25/0017* (2013.01); *A61M 2025/0166* (2013.01); *A61M 2025/09008* (2013.01)

(58) Field of Classification Search
None
See application file for complete search history.

(56) References Cited

U.S. PATENT DOCUMENTS 6,535,764 B2 3/2003 Imran et al.
7,387,626 B2 6/2008 Edwards et al.
(Continued)

FOREIGN PATENT DOCUMENTS

WO 2007126632 A2 11/2007
WO 2008017071 A2 2/2008
(Continued)

OTHER PUBLICATIONS

Extended European Search Report re EP App. No. 19877888 dated Jun. 21, 2022.
(Continued)

*Primary Examiner* — John R Downey
*Assistant Examiner* — Anant A Gupta
(74) *Attorney, Agent, or Firm* — Brooks Kushman P.C.

(57) ABSTRACT

Embodiments of the invention provide apparatus, systems and methods for stimulating tissue in the urinary tract to initiate or facilitate urination. One embodiment provides an external urinary sphincter stimulation (EUSS) catheter for stimulating the external urinary sphincter (EUS), where the EUSS catheter includes nerve stimulation electrodes (NSES) for delivering current to nerves within or around the EUS in order to relax the EUS prior to urination. Other embodiments provide a system for stimulating the EUS including the EUSS catheter and a controller operatively coupled to the EUSS catheter, where the controller includes a pulse generator for delivering current to the NSES. Other embodiments provide methods for positioning the EUSS catheter in the patient's body including in the EUS using a urethral approach. Embodiments of the invention are particularly useful for initiating and/or controlling urination for patients who have lost the ability to voluntarily urinate due to neurogenic bladder dysfunction.

16 Claims, 5 Drawing Sheets

(51) Int. Cl.
  *A61M 25/00* (2006.01)
  *A61F 2/04* (2013.01)
  *A61M 25/09* (2006.01)
  *A61M 25/01* (2006.01)

(56) References Cited

U.S. PATENT DOCUMENTS

| | | | |
|---|---|---|---|
| 7,647,113 B2 | 1/2010 | Wirbisky et al. | |
| 8,168,249 B2 * | 5/2012 | Utas | A61L 29/14 |
| | | | 427/2.3 |
| 2008/0065167 A1 | 3/2008 | Boggs, II et al. | |
| 2008/0161876 A1 * | 7/2008 | Wirbisky | A61B 90/11 |
| | | | 606/129 |
| 2008/0188867 A1 * | 8/2008 | Ignagni | A61N 1/0502 |
| | | | 607/2 |
| 2009/0318990 A1 * | 12/2009 | Tomaschko | A61N 1/3625 |
| | | | 607/10 |
| 2014/0058284 A1 | 2/2014 | Bartol et al. | |
| 2014/0058588 A1 | 2/2014 | Vitet et al. | |
| 2014/0249595 A1 | 9/2014 | Chancellor et al. | |
| 2014/0309550 A1 | 10/2014 | Iglesias | |
| 2016/0051325 A1 * | 2/2016 | Hooven | A61B 18/14 |
| | | | 606/41 |
| 2017/0043156 A1 | 2/2017 | Possover | |
| 2017/0203100 A1 | 7/2017 | Imran | |
| 2017/0231547 A1 * | 8/2017 | Imran | A61N 1/0551 |
| | | | 600/554 |
| 2017/0252560 A1 * | 9/2017 | Imran | A61N 1/0514 |
| 2018/0236220 A1 * | 8/2018 | Glenn | A61N 1/0558 |

FOREIGN PATENT DOCUMENTS

| | | |
|---|---|---|
| WO | 2010107900 A2 | 9/2010 |
| WO | 2017139800 A2 | 8/2017 |
| WO | WO-2020092579 A1 | 5/2020 |

OTHER PUBLICATIONS

International search report with written opinion dated Jan. 23, 2020 for PCT/US2019/058881.

* cited by examiner

DEVICE, SYSTEMS AND METHODS FOR TREATMENT OF NEUROGENIC BLADDER

CROSS-REFERENCES TO RELATED APPLICATIONS

This application claims the benefit of and priority to U.S. Provisional Patent Application No. 62/754,433 filed Nov. 1, 2018 which is fully incorporated by reference herein for all purposes.

BACKGROUND OF THE INVENTION

1. Field of the Invention

The present invention relates to systems and methods for treating patients who have lost the ability to voluntarily control one or more bodily functions such as urination due to spinal cord injury or other neurological disorder. More particularly, embodiments of the invention relate to systems and methods for treating such patients via electrical stimulation of one more tissue sites related to control of urination. Still more particularly, embodiments relate to systems and methods for treating such patients via electrical stimulation of external urethral sphincter.

Nerves and other neural tissue in the body control how the bladder stores and empties urine. Damage to these nerves can result in a condition known as neurogenic bladder (also known as neurogenic bladder dysfunction) which is characterized by dysfunction of the urinary bladder including loss of bladder control. The condition can be caused by damage or injury to the brain, or spinal cord or the nerves from the spinal cord which innervate or signal to the organs in the urinary tract such as the sacral nerve and the pudendal nerve. Such nerve damage be the result of spinal cord injury (e.g., from a fall, car accident or battlefield injury) or diseases such as multiple sclerosis (MS), Parkinson's disease or diabetes. It can also be caused by infection of the brain or spinal cord, heavy metal poisoning, stroke, spinal cord injury, or major pelvic surgery. Symptoms of neurogenic bladder can include overactive bladder (OAB), underactive bladder (UAB), incontinence (including urge incontinence), and or obstructive bladder, in which the flow of urine is blocked.

Most commonly, patients suffering from spinal cord injuries can lose not only the ability to voluntarily control urination, but also the ability to sense when the bladder is full. Such patients have usually had to rely on the chronic use of a urinary drainage (Foley) catheter which is placed through the urethra and has a distal tip residing in the bladder. Such Foley catheters present a constant risk of infection which is exacerbated by the frequent need to exchange a clogged catheter for a new catheter. Moreover, Foley catheters usually drain into a bag which the patient must carry when away from home or a treatment facility. The need to carry the drain bag is a significant burden to many patients.

To at least partially overcome the above problem for treating neurogenic bladder, very promising new systems have been proposed which allow patients and their caregivers to selectively stimulate the pudendal nerves to control voiding of the bladder. Such systems can eliminate the need for Foley catheters and are described, for example, in US Patent Publication No. 2014/0249595, the full disclosure of which is incorporated herein by reference for al purposes.

While a significant advance, such pudendal nerve stimulation systems require surgical implantation of stimulation electrodes near the pudendal nerve which is typically done by access through the patient's buttocks. There are a number of drawbacks to such an approach. First, the procedure is very invasive and results in the patient being non-ambulatory for an extended period along with the risk of surgical infection which is exacerbated by being done in the buttocks area. Also, the pudendal nerve can be difficult to locate in the surgical field via a buttocks approach. Further, such surgeries are not always successful. In particular, the electrodes may come off or cause damage to the nerve requiring removal and/or replacement surgery.

For these reasons, it would be desirable to provide improved systems and methods for initiating and controlling urination via stimulation of other tissue than the pudendal nerve and/or to do so using a less invasive approach. It would be further desirable to provide devices, apparatus and systems which are suitable for minimally invasive implantation, as well as methods for positioning and implanting such systems. At least some of these objectives will be met by the inventions described hereinafter.

2. Description of the Background Art

US 2014/0249595, has been described above. See also US 2014/0058284; US 2014/0058588; US 2014/0309550; and US2017/0203100.

SUMMARY OF THE INVENTION

Various embodiments of the invention provide devices, systems and methods for initiating and controlling bodily elimination functions such as urination and defecation. Many embodiments of the invention provide devices, systems and methods for initiating and controlling urination via stimulation of various types of bodily tissue and structures such as nerve, muscle, sphincter and vascular tissue. Particular embodiment provide devices, systems and methods for doing so by stimulation of tissue typically other than the pudendal nerve. Further, particular embodiments provide a stimulating device such as a catheter or lead for stimulating tissue such as the external urinary sphincter (EUS) so as to initiate and/or control urination. Such devices, systems and methods are particularly useful for treatment of patient having neurogenic bladder who have lost the ability to voluntarily initiate and/or control urination.

In a first aspect, embodiments of the present invention provide a stimulating catheter or other stimulating device for stimulating the EUS and/or to control urination or other urinary function, referred to hereinafter as an EUS stimulating or "EUSS" catheter. Other embodiments of the device (herein a stimulating device or EUS stimulating device) may correspond to a lead or other elongated member which have one or more features of the catheter described herein. The EUSS catheter includes a catheter body having a proximal end, a distal end, an anchoring element (also referred to as an anchor) positioned at the proximal end, at least one nerve stimulating electrode, an electrical plug connector (also referred to as an electrical connector, connector element or connector), and a detachable or otherwise removable distal portion, having a tissue-penetrating distal end. In various embodiment, the removal distal portion is configured to function as a tether for pulling portions of the EUSS catheter through and/or out of the patient's tissue and is thus referred sometimes herein as a "distal tether portion", "distal tether" or simply a "tether". Also, in specific embodiments, the anchoring element corresponds to a ball tip. The ball tip or other anchoring element may comprise a polymer or an electrically conductive metal, such as platinum or stainless steel. When comprising an electrically conductive metal or other material, the ball tip or other anchoring element may be used as an electrode in conjunction with one or more nerve stimulation electrodes positioned along the catheter body distally of the ball tip so as to provide for a bipolar configuration of nerve stimulation electrodes and current delivery to the EUS.

The EUSS catheter is configured to be advanced into the patient's urethra, typically through a lumen of a guiding catheter, and then through the urethra wall and into the EUS by means of the tissue penetrating end of the removable distal tether portion. The guiding catheter will typically have a guiding lumen with an exit port which is oriented to deflect the tissue penetrating end of the nerve stimulating electrode laterally. Thus, by properly axially and rotationally positioning the guiding catheter within the urethra, the tissue penetrating end of the distal tether portion of the EUSS catheter can be advanced (e.g., steered) in a direction toward a desired exit location within the urethra.

Once the tissue penetrating end has passed through the urethral wall, the catheter body and distal, portion of the EUSS catheter together have sufficient column strength to push and advance the tissue penetrating end through tissue until the tissue penetrating end of detachable distal tether portion exits through an external tissue (skin) surface, typically in the patient's perineum or buttocks area. The EUSS catheter is further configured to have sufficient tensile (pull) strength to be drawn distally by the detachable portion to lodge the ball tip into the EUS or surrounding tissue.

The at least one nerve stimulation electrode is positioned on the catheter body near the proximal end and is configured to deliver stimulation current to nerves leading to and/or innervating the EUS to relax the EUS sufficiently to allow the flow of urine into the urethra. The electrical plug connector(s) are positioned near the distal end of the catheter body and are electrically coupled to the at least one nerve stimulation electrode and are configured to be connected any one of a controller, a pulse generator, or other electrical stimulator which is either implanted or external to the patient's body. The electrical connector(s) are configured to be advanced into tissue of the patient's buttocks/perineum region (as the tissue penetrating end is advanced through the patients buttocks/perineum region) and then into subcutaneous tissue in the patient's back area where it (they) may be connected to a mating connector for the pulse generator or other stimulator. In particular embodiments, the electrical connector(s) on the catheter may comprise a series of conductive elements such as conductive metal rings or strips which are electrically coupled to each of the nerve stimulation electrodes by elongate conductors running axially through the catheter body. The elongate conductors are typically metal wires which contribute to the tensile strength of the catheter body. Optionally, the catheter body may be further reinforced with aramid (e.g., Kevlar®) or other polymer or metal filaments to enhance catheter body's tensile strength which is an advantage when the catheter body is pulled into a desired tissue location within the patient's body so as to anchor the ball tip as described herein. Specifically, such reinforcement facilitates pulling the catheter by its distal portion so as to exert sufficient force tensile force to anchor the ball tip or other anchor in tissue such at the EUS or other tissue site.

The removable distal portion of the EUSS catheter or distal tether portion, will typically comprise a wire or tube comprising a nickel-titanium (e.g., Nitinol®) or other superelastic metal or like material allowing the distal tether portion to bend and flex as it is advanced out of a side aperture in the guiding catheter while retaining sufficient column strength to be advanced into the urethral wall tissue. The tissue-penetrating end of the removable distal tether portion will typically be stiffened to enhance penetration into the urethral wall when being advanced into the EUS and then into or through the patients buttocks or perineum area so that it exits out of tissue in this area. Stiffening may be achieved through various metal working methods known in the art or by varying one or more of the diameter or composition of the tissue penetrating end.

Once the tissue-penetrating end of the removable distal tether portion exits the skin surface, the physician can pull on the distal end of the removable portion to draw the catheter body of the EUSS catheter through the urethral wall until the ball tip or other anchoring element lodges in the urethral wall and/or into tissue in or adjacent the EUS, thus properly locating the stimulation electrode(s) so as to stimulate the EUS and/or pudendal nerve to cause relaxation of the EUS (e.g., by blocking signals from the pudendal nerve causing contraction of the EUS). The distal tether portion can be then be removed from the catheter body by any one of various detachable mechanisms and/or means known in the catheter and medical leads art. For example, the distal tether portion may be configured to be cut from the catheter body using conventional surgical cutting tools.

In exemplary embodiments, the at least one nerve stimulation electrode comprises at least two nerve stimulation electrodes, and the at least two nerve stimulation electrodes may be axially spaced-apart along a length of the EUSS catheter body distal to the proximal anchor. Alternatively, a first nerve stimulation electrode may be positioned on one side of the catheter body and a second nerve stimulation electrode may be positioned on an opposite side of the catheter body. In still further embodiments, the at least one nerve stimulation electrodes may comprise at least three nerve electrodes, and in some cases the at least one nerve stimulation electrodes may comprise at least four nerve electrodes with additional numbers contemplated.

In exemplary embodiments, the EUSS catheter will include at least two or more stimulation electrodes which typically will be configured to deliver bipolar current to the EUS, though monopolar configurations are also considered. The nerve stimulation electrodes may be positioned on various locations on the catheter body. For example, a first nerve stimulation electrode may be disposed on one side of the catheter body and a second nerve stimulation electrode may be disposed on the opposite side of the catheter body. According to other embodiments, the electrodes may be axially spaced apart along a length of the EUSS catheter, for example, a first nerve stimulation electrode may be located at a first axial location on the catheter body and a second nerve stimulation electrode may be located at a second axial location on the catheter body. Typically, such axially spaced-apart electrodes will comprise ring electrodes which at least partially circumscribe the catheter body. The width of the electrodes can be in the 1-3 mm range and the spacing between electrodes can be in the 1-5 mm range. Other electrode shapes are also contemplated including partial ring shaped (e.g., semi-circular), which may be distributed along a circumference of the EUS catheter body.

In preferred embodiments, the EUS catheter body will include four or more ring or other form of stimulation electrodes which are axially spaced apart along a length of the catheter or lead. All or a selected number of the electrodes may be energized concurrently and/or consecutively in pairs to effect bipolar stimulation with current from the pulse generator or other current source. The number and spacing of the stimulation electrodes on the catheter can be configured so produce a selectable electric field volume within or adjacent the EUS so as stimulate the EUS to relax upon energization of the stimulation electrodes. In related embodiments, the number of electrodes energized with current to stimulate the EUS can also be selected so as to produce the desired electric field volume within or adjacent the EUS. In various embodiments, the selection of stimulation electrodes to energize may be implemented by means of a controller (or other logic resources) described herein which is operably coupled to the EUS stimulation catheter as well as the pulse generator or other current generation means.

In specific instances, the anchoring element may have a ball shape with a diameter larger than the diameter of the proximal end of the catheter body. Further, in specific instances, the anchoring element is itself electrically conductive and configured to act as a nerve stimulation electrode. In other instances, the methods may utilize a plurality of stimulating electrodes and an equal plurality of connector elements, and both the stimulating electrodes and the connector elements may comprise ring conductors. In still other aspects, the present invention provides systems using any of the catheter constructions described herein. The system may further include a pulse generator configured to deliver high frequency current to the at least one nerve stimulation electrode. The pulse generator is configured to deliver current at a frequency above about 4 kHz, amperage below about 15 mA, and a voltage in a range from about 40V to 60V. Often, the pulse generator will be configured to deliver bipolar current to at least first and second electrodes on the catheter body.

In a second aspect, embodiments of the invention provide systems for controlling urination in a patient who has lost the ability to urinate due to injury (e.g., a spinal injury), disease or other cause. In one embodiment of such a system, the EUSS catheter or lead is coupled to a controller to control one or more aspects of the delivery of current to the EUS and the sacral nerves by the EUSS catheter. The controller may correspond to one or more of a microprocessor or other logic resources either digital or analogue. It may include its own electrical power source such as chemical storage battery or can be configured to be coupled to an electrical power source such as a battery or an AC source.

The controller may also include or be operatively coupled to a pulse generator or other electrical stimulator for generating various current waveforms to cause one or more physiological responses involved in the urination process. Embodiments of such a system are configured to deliver an electrical waveform to nerves adjacent or within a patient's EUS to stimulate and/or block nerve impulses going to the patient's EUS so as to cause a physiological action involved in the urination process. Such actions may include one or more of opening of patient's urethra, contraction of the bladder, and relaxation of the bladder. Specific characteristics of the wave form which may be selected for producing such actions include one or more of frequency, voltage, current etc. Typically though, frequency is the characteristic which is used to produce a specific physiologic action. For example, high frequencies (above 4 khz, such as in a range of 4 to 25 kHz, with a preferred value of about 5 or 6 khz) can be used to cause opening of the urethra by blocking signals from the pudendal nerve which cause the EUS to remain closed, while lower frequencies are used to contract the bladder (e.g., 10 to 50 Hz, with a preferred value of about 20 hz), and very low frequencies are used to relax the bladder (e.g., 1 to 15 Hz, with preferred value of about 5 Hz) to cease urination. The system may also include or be combined with a sacral nerve stimulation (SNS) catheter or lead having electrodes which are positioned in electrical contact with the patient's sacral nerve to deliver current in the form of an electrical wave form to stimulate the patient's bladder to contract or relax.

In specific embodiments, the controller is configured to deliver current to the EUS in the form of a high frequency electrical waveform using frequencies as described above in order to block signals from the pudendal nerve to open the urinary sphincter and allow the flow of urine through the urethra. The controller may also be configured to deliver a low frequency current to the sacral nerve in order to cause contraction of the bladder and a very low frequency to cause relaxation of the bladder and cease urination using frequencies as described above. In many embodiments, the controller is configured to deliver the low frequency and high frequency waveforms simultaneously, typically being initiated and terminated at about the same time. However, other embodiments contemplate initiating the high frequency waveform first so as to open the urinary sphincter and then, after a select period of time (e.g., 0.5 to 5 seconds), concurrently delivering the low frequency waveform to contract the bladder so as to initiate urination.

Desirably, the amperage for one or more of the three waveforms (e.g., high, low and very low frequencies described above) is below about 15 mA more preferably below about 4 mA, and the voltage is in the range from about 40V to 60V. The controller/pulse generator will typically be configured to deliver bipolar current to one or more electrode pairs on the EUS or SNS catheters but, in other instances, could be configured to deliver monopolar current. The controller can also be configured to limit the total amount of delivered electrical energy/power to stay below that which would injure, burn, or damage tissue near the nerve stimulation electrodes. To that end, in particular embodiments, the controller may be configured to receive an input from a temperature or other sensor positioned on the catheter proximal end and utilize that input to control or otherwise regulate the delivery of electrical energy to the electrodes so as to stay below a selected temperature threshold which would injure or otherwise damage tissue near the catheter tip. In these and related embodiments, the controller may include a temperature control algorithm, such as a P, PI or PID algorithm, or the like as is known in the art. Typically, the control algorithm will be implemented using an electronic instruction set embedded in a processor or other logic resources incorporated into the controller.

The system will also typically include an implantable sensor configured to sense information corresponding to a degree of filling or fullness of the patient's bladder. Such an implantable sensor will typically correspond to a pressure or force sensor configured to measure or sense pressure or fullness of the bladder. The sensor is operatively coupled to the controller as so provide information on bladder fullness which may then be used by controller to determine when to initiate urination and to stimulate one or both of the EUS and sacral nerve.

In a third aspect, embodiments of the invention provide a method for positioning a nerve stimulation catheter, lead or other device (such as any of the EUSS catheter embodiments described elsewhere herein), in urinary tissue of a patient so as to stimulate and open the EUS to allow passage of urine in patients who have lost the ability to voluntarily urinate. The method comprises providing a guiding catheter configured to be advanced into the urethra of a patient and an EUSS catheter. The guiding catheter includes at least one lumen for advancement of the EUSS catheter.

In many embodiments, the guiding catheter may include a two or three arm adapter at its proximal end with one arm of the adapter connected to a lumen for advancing the EUSS catheter lumen, a second arm connected to a lumen for introducing a liquid or gas to inflate a bladder anchoring balloon described elsewhere herein, and a third arm connected to a lumen for passage of fluid into and out of the bladder. According to some embodiments, the guiding catheter lumen through which the EUSS catheter is advanced extends continuously from the adapter to the distal end of the guiding catheter. In other embodiments, the guiding catheter lumen through which the EUSS catheter is advanced terminates in a lateral deflection port or aperture which exits on the side of the guiding catheter at a location proximal of the distal tip by a selected distance typically from 1 cm to 15 cm. In such and related embodiments, the guiding catheter can include an inflatable anchoring balloon or other anchoring means circumscribing a distal portion of the guiding catheter. Actuation of the anchoring means, typically inflation of the anchoring balloon, anchors the distal portion of the guiding catheter in the bladder. The aperture for exit of the EUSS catheter (also referred to as an exit aperture) is placed proximally to the anchoring balloon a selected distance such that it is an approximate alignment to the portion of the urethra near the EUS when the guiding catheter is anchored in the bladder. That is, the balloon or other anchor is positioned in the bladder so that the exit aperture aligns with the section of the urethra containing the EUS. In some embodiments, the guiding catheter can be manually manipulated by the physician to facilitate the desired alignment. After the EUSS catheter or other EUSS device has been advanced through the guiding catheter and lodged in or adjacent to tissue of urethral wall. the anchor may be disengaged (e.g., by deflation) and the guiding catheter removed from the urethra. As described below, according to some embodiments, removal may be facilitated by the use of radio-opaque or other medical imaging markings.

The guiding catheter is advanced into the urethra a selected distance such that the distal end is near the portion of the urethra surrounded by the EUS. This may be facilitated by placement of radiopaque or other markings on the guiding catheter in order to visualize its position under fluoroscopy or other medical imaging modality. The EUSS catheter is then advanced through a lumen of the guiding catheter until the distal tether portion exits and the tissue penetrating end of the distal tether portion of the catheter penetrates the urethra into tissue adjacent the EUS. The distal tether portion continues to be advanced, typically by pushing on the proximal portion of the EUSS catheter, until the distal tip exits through external tissue in the perineum area of the patient's body. Positioning is desirably (but not necessarily) done using a medical imaging modality such as ultrasound or fluoroscopy in order to visualize the position of the stimulation catheter and the guiding catheter. For embodiments where the guiding catheter has an anchoring balloon and proximally placed aperture, the distal portion of the guiding catheter is advanced into the bladder, and the anchoring balloon is inflated to anchor the guiding catheter in the bladder (which may be pulled back slightly once the balloon is inflated). Then, once the guiding catheter is anchored, the EUSS catheter is advanced out of the aperture so the tissue penetrating tip goes through the urethral wall and into the EUS or surrounding tissue.

For either of the above approaches (e.g., anchored and non-anchored guiding catheters), the distal tether of the EUSS catheter is then pulled out of the patient's body, typically at a location in the perineum area, until the ball tip or other anchoring element is lodged in tissue in or adjacent tissue of the urethral wall and such that the plurality of stimulating electrodes are positioned in tissue adjacent the EUS to directly stimulate the EUS when stimulating current is delivered through the electrodes. Also, in some embodiments the physician may tactilely sense a resistance to drawing the distal tether portion of the EUSS catheter from the perineum area when the proximal anchor has become lodged in or adjacent to tissue of urethral wall. This may be done by hand or using a force gauge or other force measurement instrument known in the medical arts. In use, such approaches advantageously provide a more reliably approach for assessing that the ball tip or other anchoring element is adequately lodged in tissue in or adjacent tissue of the urethral wall so as to remain fixed for an extended period of time, e.g., years.

An exposed portion of the EUSS catheter may then be pulled out of tissue and next tunneled underneath tissue in the patient's buttocks and/or back area and advanced such that the distal end comes out at a selected tissue site, typically a tissue pocket formed in the patient's back, abdominal area, or pectoral area. Such advancement is typically facilitated by the use of a tunneling tool which may be customized (e.g., in dimensions and shape) for use with embodiments of the EUSS catheter. The tissue penetrating distal portion of the lead catheter is then removed from connector portion of the lead catheter leaving the connector end free for connection to an implanted device such as a pulse generator and/or other wire. Removal can be accomplished by pulling and/or cutting of the tissue penetrating distal end. The connectors at the distal end of the catheter body are then electrically connected to the pulse generator (or other implanted signal generation device) and/or a lead which makes an electrical connection to the pulse generator or other electrical stimulator. Connection can be accomplished using a variety of connection means and methods known in the art including for example a snap fit, crimping or other like connection means. After the connector is connected to the controller, the integrity of the connection can be tested by sending a test signal from the controller or like device to the EUSS catheter and observing or otherwise determining if there is relaxation of the patient's external urinary sphincter.

After implantation of the EUSS catheter, a second stimulation catheter and/or lead can optionally be implanted in tissue with its electrode(s) positioned on or near the sacral nerve and a proximal portion of that catheter connected to the pulse generator. The second stimulation catheter is known as a sacral nerve stimulation catheter or SNS catheter and can be used to stimulate the sacral nerve to cause bladder contraction for voiding of urine from the bladder. In one or more embodiments, the SNS catheter can be used in combination with the EUSS catheter to stimulate nerves and/or tissue to initiate and control urination in the patient by causing i) relaxation of the EUS to open the patient's urethra to allow for the passage of urine; ii) contraction of the bladder to void urine from the bladder; iii) relaxation of the bladder; and iv) contraction of the EUS to close the patient's urethra. Similar to the testing of the EUSS catheter, after connection of the SNS catheter to the pulse generator (or other electrical stimulator) the integrity of the connection can be tested by sending a test signal from the pulse generator to the sacral nerve and observing or otherwise determining if the bladder has contracted. Also, after implantation of the catheter, the incisions in the patients buttock or back used for placement of the EUSS and SS catheters can be closed by suturing or other closure method known in the surgical arts.

In a fourth aspect, the embodiments of the invention provide a method for initiating and controlling urination in a patient having compromised bladder function (e.g., due to neurogenic bladder) in which the external urinary sphincter is directly stimulated using embodiments of the EUSS catheter or lead or device described herein so as to open to the EUS for the passage of urine. Desirably, the electrical stimulation has a frequency in a range from about 4 kHz to 30 kHz, more preferably in a range from about 4 to 25 kHz and even more preferably, in a range of about 5 to 6 kHz. This stimulation can then be supplemented by electrical stimulation of the sacral nerve to cause contraction and subsequent relaxation of the bladder to expel urine from the bladder to initiate urination and then cease once the bladder is emptied. Low frequency current can be used to stimulate the sacral nerve in order to cause contraction or relaxation of the bladder and very low frequency current to cause relaxation of the bladder and cease urination. The low frequency current may have a frequency in a range from about 10 Hz to 50 Hz, with a preferred value of about 20 Hz. The very low frequencies used to relax the bladder may be in the range of about 1 Hz to 15 Hz, more preferably in a range from about 4 to 6 Hz, with a preferred value of about 5 Hz. Such sacral nerve stimulation may be accomplished using a sacral nerve stimulation (SNS) catheter or lead having electrodes which are positioned in electrical contact with the patient's sacral nerve to deliver current in the form of an electrical wave form to stimulate the patient's bladder to contract or relax.

For a fuller understanding of the nature and advantages of the present invention, reference should be made to the ensuing detailed description taken in conjunction with the accompanying drawings. The drawings represent embodiments of the present invention by way of illustration. Accordingly, the drawings and descriptions of these embodiments are illustrative in nature and not restrictive.

DETAILED DESCRIPTION OF THE INVENTION

Various embodiments of the invention provide devices, systems and methods for initiating and controlling urination in patients who have lost the ability to voluntarily urinate due to neurogenic bladder or other related condition. Many embodiments provide devices, systems and methods for electrical stimulation of the urinary tract including direct stimulation of the external urethral sphincter (EUS) and bladder to initiate and control urination. Particular embodiments provide catheters, leads or other devices for stimulating the EUS and bladder to initiate and control urination and systems and methods for positioning the leads in or adjacent such tissue using a urethral approach. In use, such embodiments provide novel minimally invasive devices and method for positioning stimulation leads to control urination in patients who lack such control while minimizing the risks and complications from invasive surgery. Related embodiments provide methods for positioning such catheters or leads adjacent the EUS, sacral nerve or other location in the patient's body so as to initiate and/or control urination. As used herein the term, "about" means within ±10% of a stated property, dimension, or other value and, more preferably, ±5% of the stated value. Also, as used herein, the term "substantially" means within ±10% of a stated property or quality and where appropriate within a numerical value of a stated property or quality, more preferably, ±5% of the stated property or quality. For qualitative properties or qualities such as a pain or injury "substantial" means below that which is overtly and repeatedly perceivable by the patient or medical professional.

Figure 1A:
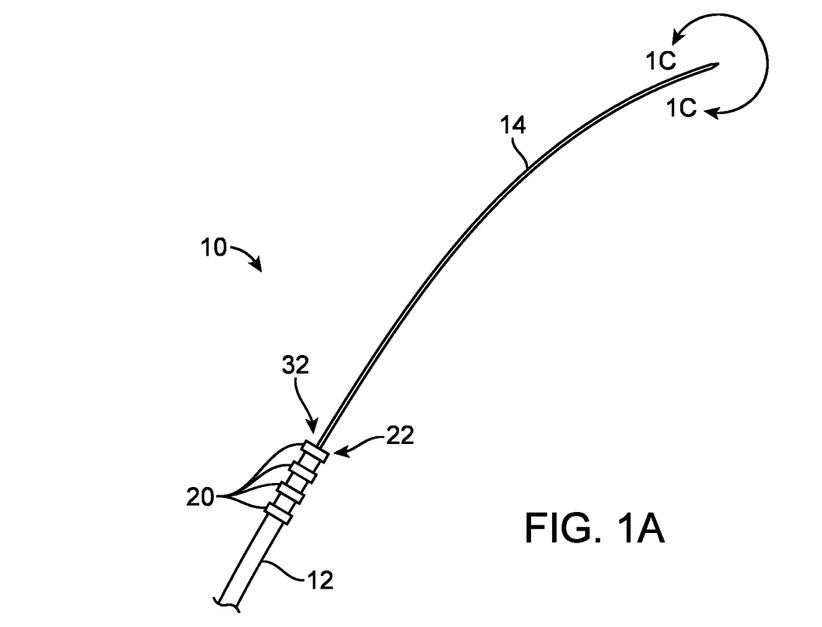
FIG. 1A illustrates an embodiment of an external urethral sphincter stimulation (EUSS) catheter constructed in accordance with the principles of the present invention.
Figure 1B:
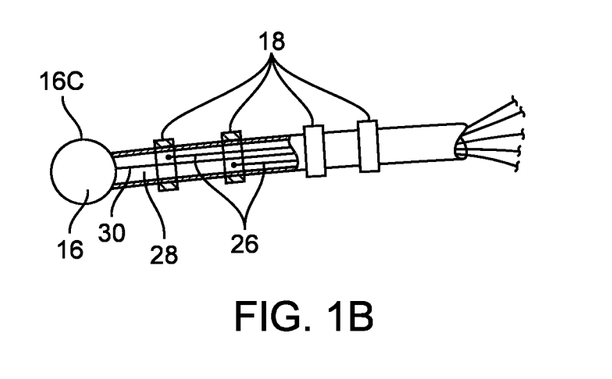
FIG. 1B is a detailed view of a proximal portion of the EUSS catheter of FIG. 1A including nerve stimulation electrodes and an anchoring element shown in partial cross-section.
Figure 1C:
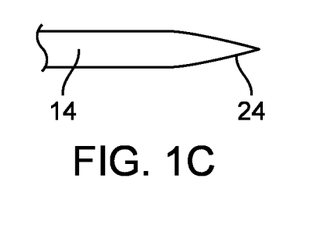
FIG. 1C is a detailed view of a distal tip of removable, distal portion of the EUSS catheter taken at line 1C-1C of FIG. 1A.

Referring now to FIGS. 1A-C, an exemplary embodiment of an EUSS catheter 10 constructed in accordance with the principles of the present invention will typically comprise a catheter body 12 having a proximal and distal end 21 and 22 respectively (distal end 22 also being referred to and/or encompassing a distal tip 22). The catheter body is detachably connected at its distal end to a distal portion 14 also referred to as a distal tether 14 or tether 14. The catheter body 12 includes a proximal anchor 16 (also referred to as an anchor element 16) at its proximal end 21, a plurality of stimulating electrodes 18 immediately distal to the proximal anchor 16. The catheter body 12 also typically includes a plurality of electrical connectors 20 at a distal portion of the catheter body which are operatively coupled to the stimulating electrodes 18 as is described below. Catheter body 12 may be configured to have various properties known in the catheter arts (e.g., pushability, trackability, etc.) allowing it to be advanced and track through a guiding catheter and then pulled by distal portion 14 through tissue so as to have anchor 16 lodge in a selected tissue location such as the EUS. Such properties can be achieved by selection of one or both of the dimensions and materials of catheter body 12. In various embodiments, catheter body 12 can be fabricated from various resilient polymers known in the catheter arts including one or more of polyethylene (e.g., HDPE, LDPE), PET, PEBAX, PTFE and copolymers thereof. Further one or more of the aforementioned polymers may be irradiated (e.g., via e-beam) for increased stiffness, flexural, tensile, compressive or torsional strength or other desired mechanical property. In some embodiments, catheter body 12 can be configured to have a compressibility or hardness similar to or less than that of tissue in which it lies adjacent or underneath (e.g., muscle or skin) such the compression of tissue around or skin above the catheter causes little or substantially no pain or discomfort to the patient. Accordingly, in these and related embodiments, catheter body 12 and or the material selected for its construction can have a Shore A harness in the range of 30 to 90, more preferably in a range of about 50 to 90.

Anchor 16 will typically have the form of a sphere, enlarged bulb or other rounded shape, though various embodiments contemplate other shapes as well including a wedge or cone shape, pyramidal and the like. It can be fabricated from rigid or semi-rigid material including metals such as stainless steel (e.g., 304v stainless steel) and rigid polymer including for example, polycarbonate, acrylic, polyether ketone (PEK). All or a portion of anchor 16 may be electrically conductive so as to delivery one or more stimulating currents described herein. Accordingly in such embodiments, anchor 16 may be fabricated from various conductive metals and/or conductive polymers known in the art. In various embodiments, anchor 16 may be structured or include various features to enhance one or more of its anchoring ability, long term biocompatibility and conductivity. For example, in one or more embodiments anchor 16 may include a drug eluting coating or other surface layer 16c configured to reduce the attachment of cells, platelets or proteins (e.g., collagen) to the surface of anchor 16. Anchor 16 may also include a surface layer or coating configured to reduce the deposition and/or precipitation of minerals in urine onto the anchor surface. Such layers or coatings may correspond to a PTFE or other perfluoropolymer known in the biomaterial and/or polymer art. In additional or alternative embodiments, anchor 16 can also be configured when placed in or adjacent the external urinary sphincter or EUS it does not significantly interfere with the function of including the ability of the EUS to contract around the urethra so to prevent the flow of urine or to relax so as to allow the urethra to open. This can be accomplished by selection of one or more of the size and shape of the anchor 16. In particular implementation for achieving such a function anchor 16 can have a spherical or spherical like shape such as oval. Also the volume of the anchor 16 can be selected to be below a selected percentage of the total volume of the EUS. In various embodiments the volume of anchor 16 can be kept below about 25% of that of the EUS, more preferably below about 20%, still more preferably below about 10% and even still more preferably below about 5%. In use, such embodiments provide the advantage of allowing for the long-term implantation of catheter 10 for initiation and control of urination in the patient without compromise of the function of the EUS including its function in the control or urination and maintaining urinary countenance in the patient. Also in specific implementations the size of the patients EUS can be predetermined using medical imaging (e.g., ultrasound imaging) or by other means and then anchor 16 can be custom fabricated relative to the determined volume of the EUS so as to stay below a selected percentage of the EUS volume.

A discussion of connector 20 will now be presented. Connectors 20 (also referred to as electrical connectors 20) are configured to electrically couple stimulation electrodes 20 to a pulse generator such as pulse generator 70 and may be positioned at various locations along catheter body 12. In various embodiments, connectors 20 may comprise a series of conductive elements such as conductive metal rings or strips disposed on or otherwise coupled to catheter body 12. According to one or more embodiments, a plurality of connectors 20, typically equal in number to the number of stimulating electrodes 18, may be located at or near the distal end 22 of the catheter body 12 just proximal to a proximal end of the distal tether 14. However, other positions for connectors 20 closer to electrodes 18 are also contemplated. In particular embodiments, each of the stimulating electrodes 18 is electrically coupled to a corresponding connector 20, typically by a single, isolated wire or other conductor 26 located in an inner lumen 28 of the catheter body 12. Optionally, a high strength polymer filament such as an aramid (KEVLAR) filament or other elongated reinforcement element 30 can be provided to connect the proximal anchor 16 to the distal end 22 of the catheter body 12 to provide for enhanced tensile strength of the catheter allowing the catheter to be pulled through tissue by distal tether 14. Other reinforcement elements may include one or more of a rigid polymer member, stiffening wire or braided section. As will be described in more detail below, the catheter body 12 is implanted by pulling distally on the distal tether 14 which places a significant axial stress on the catheter body. Use of reinforcement element 30 provides the advantage of enhances the dimensional stability of the catheter body when subjected to such stress. Further, use of an aramid filament or other reinforcement element 30 also provides the advantage of not only allowing catheter 10/catheter body 12 to be pulled through tissue by distal tether 14, but to also do so with sufficient force to anchor proximal anchor 16 in the EUS or other selected tissue site. In particular embodiments including those for example where catheter body 10 includes a re-enforcement element 30, catheter 10 can be configured to allow the transmission of between 0.5 to 10 lbs of force on anchor 16 by pulling on distal tether 14 or a distal portion of catheter 10.

Distal tether 14 may comprise one or more of wire, a polymeric member such as polymer fiber or polymer coated wires such as a polyimide coated wire. In particular embodiments, distal tether 14 comprises a resilient metal wire, such as a nickel-titanium alloy, with sufficient column strength to be pushed from its proximal end through tissue and sufficient tensile strength to be pulled from its distal end to draw the catheter body 12 through tissue. A distal tip 24 of the distal tether 14 can be sharpened or otherwise configured to penetrate tissue as the tether is advanced in a distal direction through tissue. In some embodiments, not illustrated, the distal end of the tether 14 may be steerable to allow the physician to guide the tether 14 as it is being pushed through tissue. Steerability can be implemented using various technologies known in the art including use of pull wire, fluidics (including computer controlled micro-fluidic pressure), piezoelectric materials and shape memory materials.

Stimulation electrodes 18 are configured and positioned on the catheter body 12 to stimulate the EUS to block signals from the pudendal nerve so as to relax the EUS. The specific number and spacing of the stimulation electrodes 18 on catheter 12 can be configured so produce a selectable electric field volume within or adjacent the EUS so as stimulate the EUS to relax upon energization of the stimulation electrodes. In related embodiments, the number of electrodes energized with current to stimulate the EUS can also be selected so as to produce the desired electric field volume within or adjacent the EUS.

As illustrated in FIGS. 1A-1C, the stimulation electrodes are ring electrodes 18 embedded in an outer surface of the catheter body 12 and are positioned in proximity to anchor 16. Other shapes for electrodes 18 are also contemplated including a half ring (extending around half the circumference of the catheter body), circular, oval, and a strip extending along an axial length of the catheter.

In various embodiments, the stimulation electrodes 18 may correspond to electrically conductive patches radially spaced in various configurations, for example, two electrodes spaced about 180° apart, three electrodes spaced about 60° apart, four electrodes spaced about 45° etc. The specific spacing can be configured to produce a selected electric field volume in or surrounding the EUS. These electrodes may be configured as bipolar or monopolar electrodes. In the latter case, the catheter tip 22 may also include a reference electrode or an external return electrode as described herein. In the former case, the radially spaced apart electrodes may correspond to pairs of bipolar electrodes radially spaced apart, e.g., a first pair on one side of the catheter tip and a second pair radially spaced 180° from the first pair. Also, in various embodiments, the electrodes may positioned on the surface of catheter body 12 or may be recessed beneath the surface by a selected amount, for example, between about 0.0001 inch to about 0.01 inch (with specific embodiments of 0.001 inch and 0.005 inch) so as to control the depth of penetration of electrical current into tissue. Greater amounts of recess generally reduce the depth of penetration of current into tissue and thus any resulting heating.

Figures 2A, 2B:
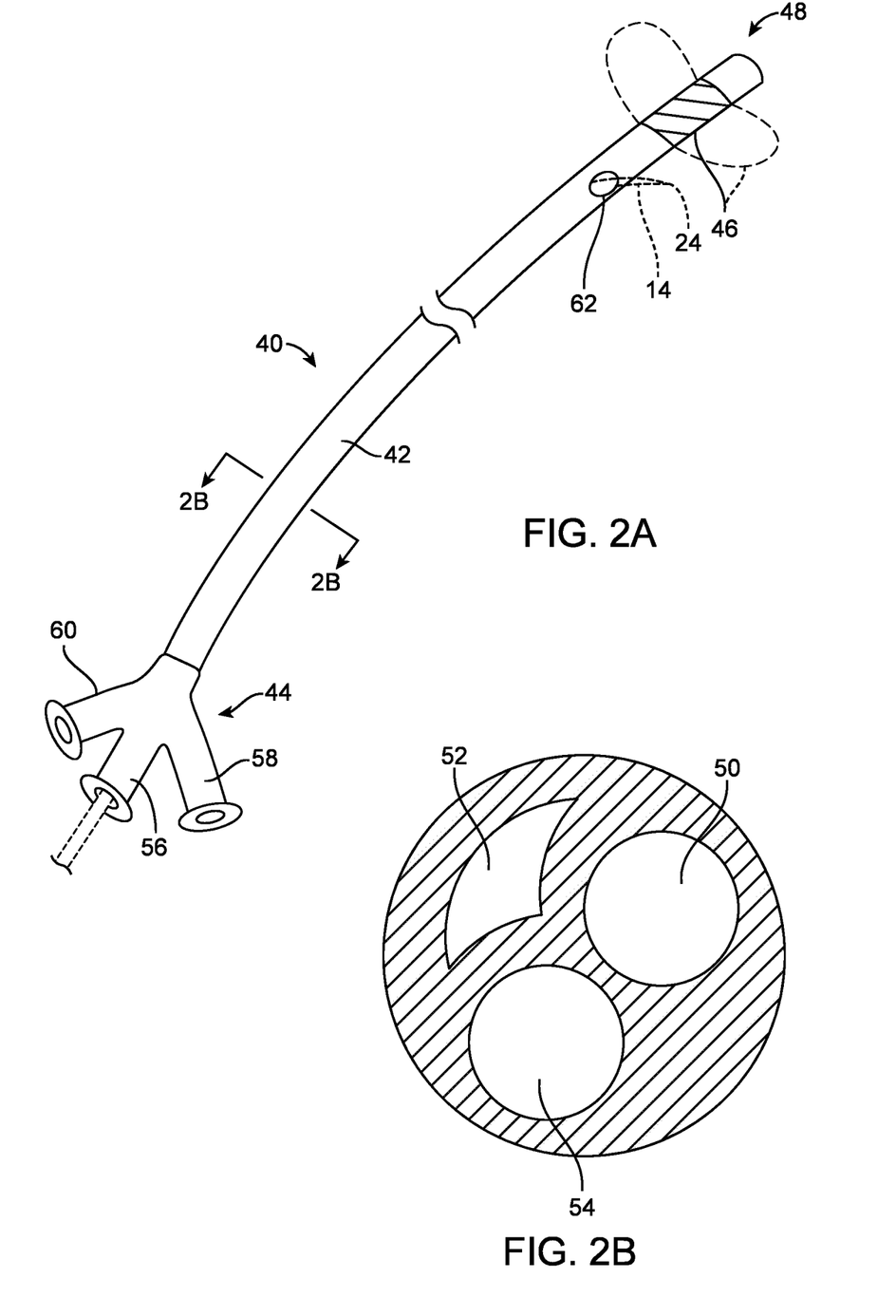
FIG. 2A illustrates a guiding catheter to be used together with the EUSS catheter of FIGS. 1A-1D as part of a urinary tract stimulation system for of placement of the EUSS catheter in the urinary tract in accordance with an embodiment of the present invention.
FIG. 2B is a cross-sectional view taken along line 2A-2A of FIG. 2A.
Figure 3A:
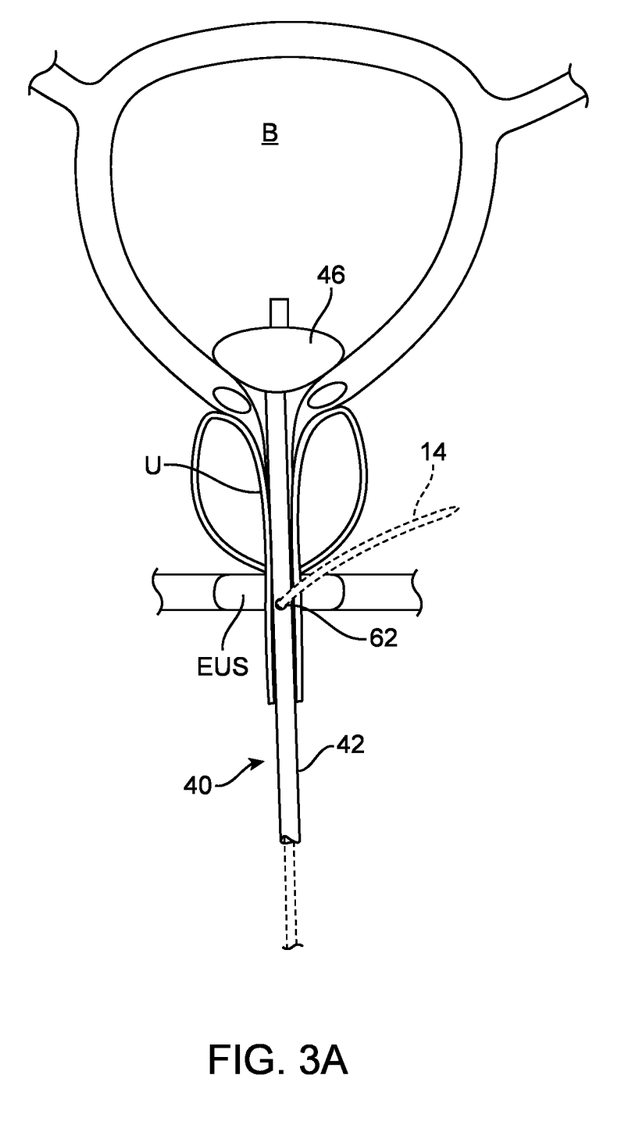
FIG. 3A illustrates the guiding catheter advanced in a male urethra with an anchoring balloon inflated in the bladder and the removable distal portion (or distal tether portion) of the EUSS catheter being advanced through the external urinary sphincter.

As shown in FIGS. 2A and 2B, a guiding catheter 40 used to advance catheter 10 in the patient's urinary tract comprises an elongated shaft 42 having a hub 44 at its proximal end and an inflatable balloon 46 at its distal end 48. The balloon is configured, when inflated, to anchor within a patient's bladder B immediately above the opening to the urethra U, as shown in FIG. 3A. The shaft is typically a multi-lumen extrusion including a lumen 50 configured to receive the EUSS catheter 10, as previously described and an inflation lumen 52. Optionally, the shaft may further include a lumen 54 for accessing the bladder. The EUSS catheter lumen 50 is accessible through port 56 in the hub 44 and terminates in an exit port 62 through a sidewall of the shaft. The exit port 62 is axially positioned on the shaft 42 so the exit port lies proximate a patient's external urinary sphincter EUS when the balloon is inflated and positioned in the bladder, as shown in FIG. 3A. The inflation lumen connects to inflation port 58 in the hub at the lumen's proximal end and to the balloon 46 at the lumen's distal end. The access lumen 54 connects through the access port 60 in the hub 44 and typically extends fully to the distal end 48 of the shat and opens in a port formed in the distal tip (hidden in FIG. 2A).

Figure 3B:
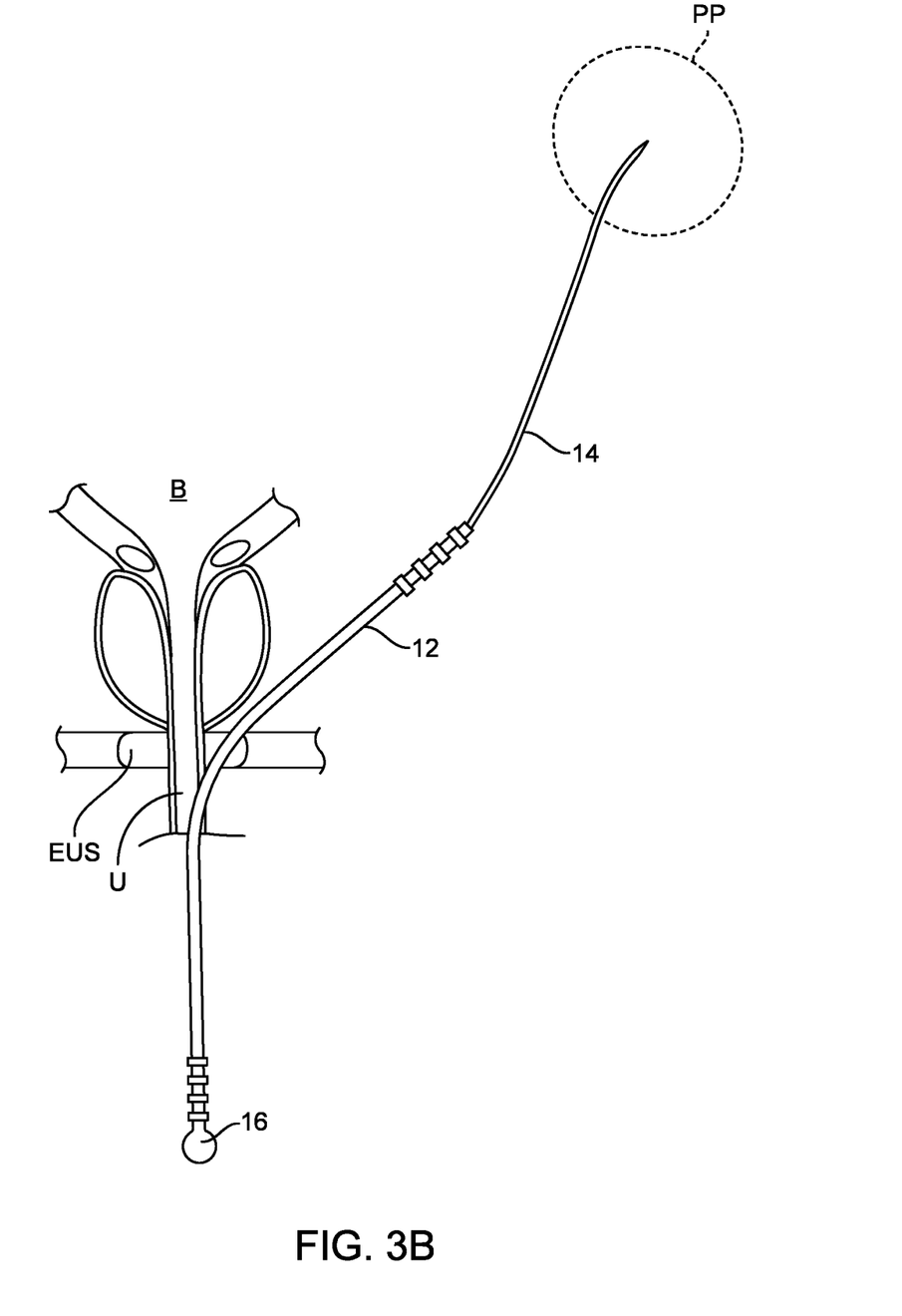
FIG. 3B illustrates the removable distal portion of the EUSS catheter being advanced further through tissue beyond the external urinary sphincter to a remote region where the pulse generator is to be implanted.
Figure 3C:
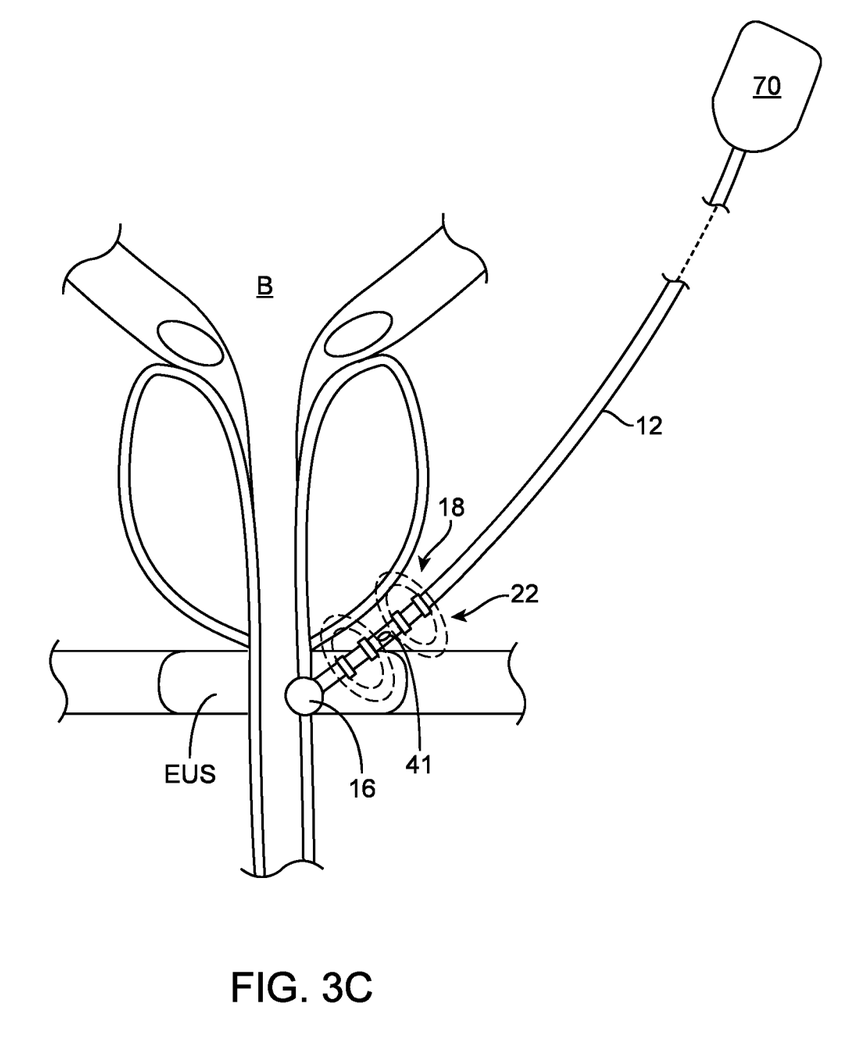
FIG. 3C is an enlarged view of the EUSS catheter in a final implantation position connected to an implanted pulse generator.

Referring now in particular to FIGS. 3A-3C, in performing implantation procedures in accordance with the principles of the present invention, the guiding catheter 40 is advanced through the patient's urethra U until balloon 46 is positioned within the bladder where it is inflated within the bladder. The physician then draws proximally on the EUSS catheter 10 (away from the bladder B) to seat the inflated balloon 46 at the bottom of the bladder above the opening of the urethra U, as shown in FIG. 3A. In this position, the exit port 62 will be position at or within the external urinary sphincter EUS.

After the guiding catheter 40 has been properly positioned with the exit port 62 at or within the external urinary sphincter EUS, the distal tether 14 of the EUS catheter 10 will be advanced so the tissue-penetrating tip penetrates into and through tissue within or adjacent to the external urinary sphincter EUS, as shown in broken line in FIG. 3A. Such advancement is typically achieved by manually pushing on a portion of the EUS catheter 10 which remains outside of the guiding catheter and available for manual manipulation. It will be appreciated, of course, that such advancement might also be achieved using a surgical robot or other automated system. Various embodiments of the invention specifically contemplate the use of elements or other features on the EUS catheter 10 to allow advancement and other manipulation by surgical robot.

Referring now to FIG. 3B, distal tether 14 is advanced until it emerges through the patient's skin, typically through the patient's perineum PP, where it can be grasped and the entire catheter 10 pulled distally until the anchor 16 engages and seats in tissue of or near the external urinary sphincter EUS, as shown in FIG. 3C. Note that the guiding catheter is not shown on FIG. 3B (to lessen complication) but would still be in place during an actual procedure. After the proximal anchor 16 is properly positioned relative to the external urinary sphincter EUS, the guiding catheter 40 may then be removed or may be left in place if continued access to the bladder B is desired.

Referring now to FIG. 3C, once the proximal anchor 16 is positioned at the external urinary sphincter EUS, the connectors 20 will be positioned to connect to a pulse generator 70 (shown in FIG. 3C) which may be external but will more often be implanted in a tissue pocket formed in the patient's back. The connectors may be advanced from the patient perineum P to the pulse generation implant location by tunneling or other conventional surgical techniques including various minimally invasive techniques known in the art and/or as described elsewhere herein.

As described herein, various embodiments of the invention contemplate delivering electrical energy into tissue of the EUS to block signals from nerves innervating the EUS (e.g., the pudendal nerve), but to do so without causing pain or injury to the patient including injury (e.g., thermal, electrical or otherwise) to one or more of the EUS, urethra or pudendal nerve. This can be accomplished through a variety of means including control of the characteristics of the electrical energy delivered including, for example, current, frequency and voltage. It can also be achieved by control of the shape and area of the electrode or other energy delivery element. For example in specific embodiments, the area of the each electrode can range from about 0.1 mm to about 100 mm, with specific embodiments of 0.5, 1, 2.5, 5, 10, 20, 25, 50, 75 and 80 mm. Larger areas can be used to reduce current density at a given electrode and in turn the degree of ohmic heating of tissue. Shapes for the electrodes which can be employed to reduce pain or injury from ohmic heating, include those having rounded edges such as circular, oval or rectangular with rounded edges (e.g., due to edge effects from higher current densities). Specific embodiments of the invention provide an inventory of electrodes or other energy delivery elements for the EUS stimulation catheters described herein, with various areas and shapes (e.g., circular, oval, etc.) selected to reduce pain and injury to the urethra and surrounding tissue including the urinary sphincter US and pudendal nerve. According to one or more embodiments, electrodes 18 etc. having selected sizes and shapes can be configured to be removably fitted (e.g., by a snap or press fit or other means known in the catheter arts) on to distal portion of the catheter including catheter distal end 22. Once fitted, the physician can then advance the catheter into the urethra and do several test deliveries of electrical energy to determine if the electrode causes any pain to the patient as well performs its intended function (e.g., to cause relaxation of the EUS). Alternatively, the electrode size and shape can be selected based on patient parameters such as size, weight, age, medical condition etc., relative to a population of those patients having those characteristics, in particular relative to the patient population in which the electrode characteristics (e.g., area, shape and material) do not cause pain or injury to the patient from ohmic heating.

According to one or more embodiments, controller 50 can also be configured to limit the total amount of delivered electrical energy/power to stay below that which would injure, burn or damage tissue near the catheter tip including the pudendal nerve. To that end, in particular embodiments, the controller 50 may be configured to receive an input from a temperature or other sensor 41 positioned on or near proximal catheter end 21 40 and utilize that input to control or otherwise regulate the delivery of electrical energy to the electrodes so as to stay below a selected temperature threshold which would injure or otherwise damage tissue near the catheter tip. In these and related embodiments, the controller may include a temperature control algorithm known in the art such as P, PI or PID or other like control algorithm. Such an algorithm can be implemented via an electronic instruction set embedded in a processor or other logic resources incorporated into or otherwise in communication with controller 50.

The foregoing description of various embodiments of the invention has been presented for purposes of illustration and description. It is not intended to limit the invention to the precise forms disclosed. Many modifications, variations and refinements of the embodiments described herein will be apparent to practitioners skilled in the art including for example those skilled in the medical implant, sensor, neurostimulation and urinary device arts. For example, examples of the device can be sized and otherwise adapted for various pediatric and neonatal applications as well as various veterinary applications. They may also be adapted for the urinary tracts of both male and female patients. Further, those skilled in the art will recognize, or be able to ascertain using no more than routine experimentation, numerous equivalents to the specific devices and methods described herein. Such equivalents are considered to be within the scope of the present invention and are covered by the appended claims below.

With regard to the drawings, it is to be understood the drawings are not necessarily drawn to scale. There may also be distinctions between the artistic renditions shown in the drawings and the actual apparatus due to drawing perspective, the drawings not necessarily being to scale, size constraints, manufacturing considerations and other factors. Also, there are multiple embodiments and/or elements of the embodiments which are not necessarily shown in the drawings which are nonetheless, contemplated by the present disclosure.

Further, elements, characteristics, or acts from one embodiment can be readily recombined or substituted with one or more characteristics or acts from other embodiments to form numerous additional embodiments within the scope of the invention. Moreover, elements that are shown or described as being combined with other elements, can, in various embodiments, exist as standalone elements. Also, for any positive recitation of an element, characteristic, constituent, feature, step etc., embodiments of the invention specifically contemplate the exclusion of that element, value, characteristic, constituent, feature or step. Hence, the scope of the present invention is not limited to the specifics of the described embodiments, examples and drawings, but is instead, limited solely by the appended claims.

What is claimed is:

1. A catheter for electrical stimulation of a patient's external urinary sphincter (EUS), the catheter comprising:
   a catheter body having a distal end and a proximal end, said catheter body sized and configured for advancement through a lumen of a guiding catheter;
   an anchoring element positioned at the proximal end of the catheter body, the anchoring element configured to anchor the proximal end in the patient's EUS or urethral wall;
   at least one nerve stimulation electrode positioned near the proximal end of the catheter body distally of the anchoring element such that the at least one nerve stimulation electrode is positioned in or proximate the EUS when the anchoring element is anchored in the EUS or urethral wall, said at least one nerve stimulation electrode being configured to deliver a high frequency current to the EUS to block signals from the patient's pudendal nerve to relax the patient's EUS;
   at least one connector element positioned on a distal portion of the catheter body and electrically coupled to the at least one nerve stimulation electrode, the at least one connector element configured to connect to a pulse generator; and
   a distal tether detachably attached to the distal end of the catheter body, the distal tether having a tissue-penetrating distal tip to penetrate the urethral wall and exit tissue on the patient's posterior as the catheter body is advanced by pushing on its proximal end, the distal tether configured to be pulled from its distal end to lodge the anchoring element in the EUS or urethral wall.

2. The catheter of claim 1, wherein the at least one nerve stimulation electrode comprises at least two nerve stimulation electrodes.

3. The catheter of claim 2, wherein the at least two nerve stimulation electrodes are axially spaced apart along a length of the catheter body distal to the anchoring element.

4. The catheter of claim 2, wherein a first nerve stimulation electrode of the at least one nerve stimulation electrode is positioned on one side of the catheter body and a second nerve stimulation electrode of the at least one nerve stimulation electrode is positioned on an opposite side of the catheter body.

5. The catheter of claim 1, wherein the at least one nerve stimulation electrode comprises at least three nerve electrodes.

6. The catheter of claim 1, wherein the at least one nerve stimulation electrode comprises at least four nerve electrodes.

7. The catheter of claim 1, wherein the anchoring element has a ball shape with a diameter larger than a diameter of the proximal end of the catheter body.

8. The catheter of claim 1, wherein the anchoring element is electrically conductive and configured to act as a nerve stimulation electrode of the at least one nerve stimulation electrode.

9. The catheter of claim 1, wherein the catheter comprises a plurality of stimulating electrodes and an equal plurality of connector elements, and wherein the at least one nerve stimulation electrode and the at least one connector element are equal in number.

10. The catheter of claim 1, wherein the catheter body has a hardness below that which causes the patient pain or discomfort when tissue adjacent or above the catheter body is compressed.

11. The catheter of claim 10, wherein the catheter body has a shore A hardness in a range from about 30 to 90.

12. A system for initiating and/or controlling urination in a patient, the system comprising:
the catheter of claim 1; and
a pulse generator configured to deliver high frequency current to the at least one nerve stimulation electrode.

13. The system of claim 12, wherein the pulse generator is configured to deliver current at a frequency above 4 kHz, an amperage below 15 mA, and a voltage in a range from 40V to 60V.

14. The system of claim 12, wherein the pulse generator is configured to deliver bipolar current to at least first and second electrodes of the at least one nerve stimulation electrode on the catheter body.

15. The system of claim 12, further comprising a guiding catheter having an exit port positioned to lie proximate the external urethral sphincter when the guiding catheter is advanced into the urethra of a patient.

16. A system for initiating and/or controlling urination in a patient, the system comprising:
the catheter of claim 1; and
a guiding catheter having an exit port positioned to lie proximate the external urethral sphincter when the guiding catheter is advanced into the urethra of a patient.

* * * * *